US007465738B2

(12) United States Patent
Jarecki et al.

(10) Patent No.: US 7,465,738 B2
(45) Date of Patent: Dec. 16, 2008

(54) COMPOUNDS USEFUL AS PROMOTERS OF SMN2

(75) Inventors: Jill Jarecki, San Diego, CA (US); Xiaocun Chen, San Diego, CA (US); Dennis James Hurley, San Marcos, CA (US); Lewis R. Makings, Encinitas, CA (US); Mark T. Miller, San Diego, CA (US); Brian Pollok, Middleton, WI (US); Jeffrey H. Stack, San Diego, CA (US); Michael A. Whitney, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/869,498

(22) Filed: Jun. 16, 2004

(65) Prior Publication Data

US 2005/0065173 A1 Mar. 24, 2005

Related U.S. Application Data

(60) Provisional application No. 60/479,064, filed on Jun. 16, 2003, provisional application No. 60/479,065, filed on Jun. 16, 2003, provisional application No. 60/479,062, filed on Jun. 16, 2003, provisional application No. 60/479,063, filed on Jun. 16, 2003, provisional application No. 60/479,024, filed on Jun. 16, 2003.

(51) Int. Cl.
*A61K 31/517* (2006.01)
*A61K 31/55* (2006.01)
*C07D 239/72* (2006.01)

(52) U.S. Cl. ............... 514/266.2; 514/266.4; 544/284; 544/291

(58) Field of Classification Search ............. 514/266.2, 514/266.4; 544/284, 291
See application file for complete search history.

(56) References Cited

U.S. PATENT DOCUMENTS

| 5,304,121 | A | | 4/1994 | Sahatjian |
| 5,534,518 | A | * | 7/1996 | Henrie et al. ............ 514/266.4 |
| 5,886,026 | A | | 3/1999 | Hunter et al. |
| 6,051,605 | A | | 4/2000 | Capiris et al. |
| 6,099,562 | A | | 8/2000 | Ding et al. |
| 6,204,267 | B1 | * | 3/2001 | Tang et al. ............. 514/252.17 |
| 2002/0137747 | A1 | | 9/2002 | Moriarty et al. |

FOREIGN PATENT DOCUMENTS

| DE | 2306374 | 8/1974 |
| EP | 204534 | 12/1986 |
| EP | 322390 | 6/1989 |
| EP | 393574 | 10/1990 |
| WO | WO 98/50370 | 11/1998 |
| WO | WO 01/42216 | 6/2001 |
| WO | WO 03/02544 | 1/2003 |

OTHER PUBLICATIONS

Brichta et. al., "Valproic acid increases the SMN2 protein level: . . . ", Human Mol. Gen., 2003, vol. 12, No.19, pp. 2481-2489.*
Jablonka, S. et al., "Axonal Defects in Mouse Models of Motoneuron Disease", J. of Neurobiology, 2004, vol. 58, No. 2, pp. 272-286.*
Berge, S.M. et al., "Review Article: Pharmaceutical Salts", *Journal of Pharmaceutical Sciences*, vol. 66, No. 1 (Jan. 1977), pp. 1-19.
Brichta, L. et al., "Valproic acid increases the SMN2 protein level: a well-known drug as a potential therapy for spinal muscular atrophy", *Human Molecular Genetics*, vol. 12, No. 19 (2003), pp. 2481-2489.
Chan, J.H. et al., "Selective Inhibitors of *Candida albicans* Dihydrofolate Reductase: Activity and Selectivity of 5-Arylthio-2,4-diaminoquinazolines", *Journal of Medicinal Chemistry*, vol. 18, No. 38 (1995), pp. 3608-3616.
Gavrilov, D.K. et al., "Differential SMN2 expression associated with SMA severity", *Nature Genetics*, vol. 20 (Nov. 1998), pp. 230-231.
Harris, N.V., "Antifolate and antibacterial activities of 5-substituted 2,4-diaminiquinazolines", *Journal of Medicinal Chemistry*, vol. 33, No. 1 (1990), pp. 434-444.
Hsieh-Li, H. et al., "A mouse model for spinal muscular atrophy", *Nature Genetics*, vol. 24 (Jan. 2000), pp. 66-70.
Kugelberg, E. et al., "Heredofamilial Juvenile Muscular Atrophy Simulating Muscular Dystrophy", *Arch. Neurol Psychiat.*, vol. 75 (1956), pp. 500-509.
Lefebvre, S. et al., "The role of the SMN gene in proximal spinal muscular atrophy", *Human Molecular Genetics*, vol. 7, No. 10 (1998), pp. 1531-1536.
*March's Advanced Organic Chemistry*, 5th Ed. Eds: Smith, MB and March, J, John Wiley & Sons, New York 2001, 4 pages.
Monani, U.R. et al., "The human centromeric survival motor neuron gene (SMN2) rescues embryonic lethality in Smn$^{-/-}$ mice and results in a mouse with spinal muscular atrophy", *Human Molecular Genetics*, vol. 9, No. 3 (2000), pp. 333-339.
Nicole, S. et al., "Spinal muscular atrophy: recent advances and future prospects", *Muscle & Nerve*, (Jul. 2002), pp. 4-13.
Parsons et al., "Intragenic telSMN Mutations: Frequency, Distribution, Evidence of a Founder Effect, and Modification of the Spinal Muscular Atrophy Phenotype by cenSMN Copy Number", *American Journal of Human Genetics*, vol. 63 (1998), pp. 1712-1723.
Periodic Table of the Elements, CAS version, Handbook of Chemistry and Physics, 75 ed.

(Continued)

*Primary Examiner*—James Wilson
*Assistant Examiner*—Tamthom N Truong
(74) *Attorney, Agent, or Firm*—Fish & Richardson P.C.

(57) ABSTRACT

The present invention relates to compounds useful as promoters of the SMN2 gene. The invention also provides pharmaceutically acceptable compositions comprising said compounds and methods of using the compositions in the treatment of Spinal Muscular Atrophy.

10 Claims, No Drawings

OTHER PUBLICATIONS

Petersen, S. et al., "Über Isatin-N-carbonsäureamide und ihre Reaktionen", Justus Liebigs Annalen Der Chemie, vol. 12 (1974), pp. 2003-2014 (English abstract on p. 2003).

*Pharmaceutical Sciences*, 16th Ed., Ed. W. Martin, Mack Publishing Co., Easton, PA 1980, 3 pages.

Rosowsky, A. et al., "Structure-activity and structure-selectivity studies on diaminoquinazolines and other inhibitors of *Pneumocystis carinii* and *Toxoplasma gondii* dihydrolate reductase", *Antimicrobial Agent and Chemotherapy, American Society for Microbiology*, Washington, DC, US, vol. 39, No. 1 (Jan. 1995), pp. 79-86.

Sorrell, T.N., *Organic Chemistry*, University Science Books, Sausalito CA (1999), 4 pages.

Unangst, P.C. et al., "(Aryloxy)alkylamines as Selective Human Dopamine $D_4$ Receptor Antagonists: Potential Antipsychotic Agents", *Journal of Medicinal Chemistry*, vol. 40, No. 25 (1997), pp. 4026-4029.

Whitlow, M. et al., "X-ray Crystal Structures of Candida albicans Dihydrofolate Reductase: High Resolution Ternary Complexes in which the Dihydronicotinamide Moiety of NADPH is Displaced by an Inhibitor", *Journal of Medicinal Chemistry*, vol. 44, No. 18 (2001), pp. 2928-2932.

Spinal Muscular Atrophy—Families of SMA Home Page [online], 2007 [retrieved on Jan. 3, 2008], 1 page. Retrieved from the Internet: <URL: www.fsma.org>.

* cited by examiner

COMPOUNDS USEFUL AS PROMOTERS OF SMN2

CROSS-REFERENCE TO RELATED APPLICATIONS

The present invention claims the benefit under 35 U.S.C. § 119 of U.S. Provisional application No. 60/479,064, filed Jun. 16, 2003, U.S. Provisional application No. 60/479,065, filed Jun. 16, 2003, U.S. Provisional application No. 60/479,062, filed Jun. 16, 2003, U.S. Provisional application No. 60/479,063, filed Jun. 16, 2003, and U.S. Provisional application No. 60/479,024, filed Jun. 16, 2003, the entire contents of each of the above application being incorporated herein by reference.

TECHNICAL FIELD OF THE INVENTION

The present invention relates to compounds useful as promoters of the SMN2 gene. The invention also provides pharmaceutically acceptable compositions comprising the compounds of the invention and methods of using the compositions in the treatment of neuromuscular disorders such as Spinal Muscular Atrophy.

BACKGROUND OF THE INVENTION

Proximal spinal muscular atrophies (SMAs) are a group of inherited neuromuscular disorders characterized by the degeneration of spinal motorneurons leading to muscular paralysis with muscular atrophy. Spinal muscular atrophy (SMA) is the second most common autosomal recessive disease (behind cystic fibrosis), occurring in approximately 1 in 6,000 live births. In SMA, the anterior horn cells in the spinal cord die, resulting in progressive muscle weakess and ultimately, in some cases, in the inability to breathe and swallow.

Because SMA exists as a broad spectrum from very severe infantile to very mild chronic forms of the disease, SMA has been classified into three main clinical types. Type 1 SMN, the severe form of Werdnig-Hoffman disease, has an onset at birth or before 6 months and death of respiratory distress usually occurs within two years, and children will never be able to sit or walk due to profound muscular weakness. Type II SMA (intermediate form) patients can usually sit but cannot walk or stand unaided (see Werdnig, G. *Psychiat*, 1894, 26, 706-744; Hoffmann, *J. Muenchen Med. Wschr*. 1900, 47, 1649-1651). Type 1 ml SMA patients (Kugelberg-Welander disease) show the first clinical signs after 18 months, evolving to a chronic course (Kugelberg, E. and Welander, L. *Arch. Neurol. Psychiat*. 1956, 75, 500-509). For each of these types of SMA, there is no known cure; rather, therapy is limited to amelioration of the symptoms produced by this insidious disease.

The gene involved in the pathology of SMA is the SMN gene. One copy of the gene, SMN1, is closer to the telomere and produces full-length transcripts, resulting in full-length and functional SMN protein. The other copy of the gene SMN2, is a homologous copy (differing from SMN1 by only 5 nucleotides); however, SMN2 transcripts are alternatively spliced, resulting in mainly truncated transcripts lacking exon 7, although some full-length transcripts are also produced. In patients with SMA, the SMN1 gene is either deleted or has point mutations, and thus these patients have a deficiency of full-length SMN1 protein. The severity of the disease is also believed to depend on the SMN2 copy number in SMA patients, since SMN2 is actually capable of producing some full-length protein. Because SMN2 is capable of producing some full-length protein, it has been suggested that promoting the activity of SMN2 would lead to the production of additional functional full-length protein in motor neuron cells, thereby minimizing or eliminating the effects of SMA. For a discussion of the genetic basis, therapies, emerging research, and diagnostic aids for SMA see, www.fsma.org (Families of Spinal Muscular Atrophy); Nicole et al. *Muscle & Nerve*, 2002, 4-13; Lefebvre et al. *Human Molecular Genetics* 1998, 7, 1531-1536; Gavrilov et al. *Nature Genetics*, 1998, 20, 230-231; Monani et al., *Human Molecular Genetics* 2000, 9, 333-339; Hsieh-Li et al. *Nature Genetics*, 2000, 24, 66-70); and references cited therein.

Despite the knowledge gained about the genetic basis of the disease, there remains a substantial need to develop therapies for the treatment of Spinal Muscular Atrophy. Because patients affected by SMA still have a copy of the SMN2 gene, it would be desirable to develop promoters of the SNM2 gene that would ultimately lead to the production of additional full-length and functional SMN protein, thus minimizing or eliminating the effects of SMA caused by the deletion of the SMN1 gene.

SUMMARY OF THE INVENTION

It has now been found that compounds of this invention, and pharmaceutically acceptable compositions thereof, are effective as promoters of SMN2 and thus are useful for the treatment of Spinal Muscular Atrophy. These compounds have the general formulae:

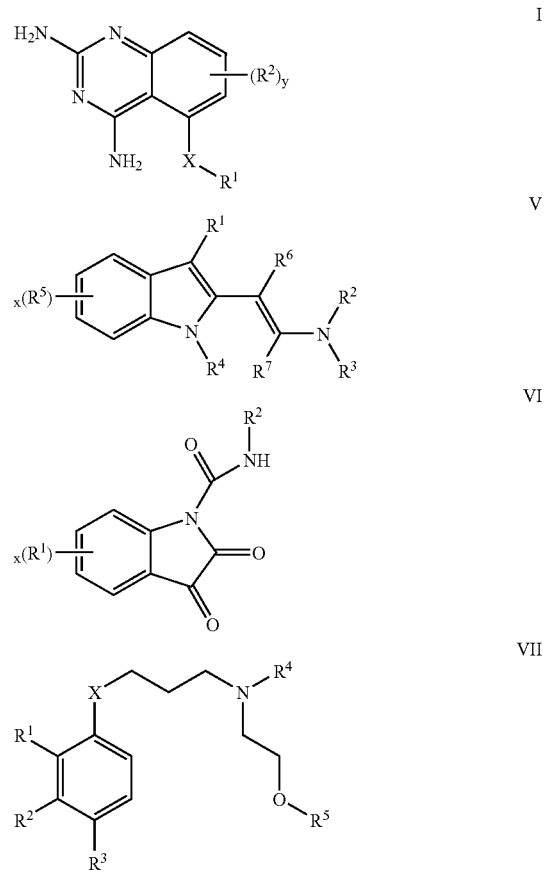

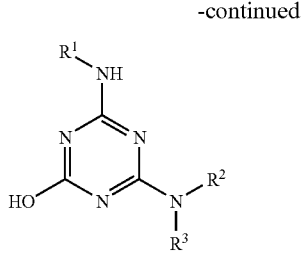

VIII or a pharmaceutically acceptable salt thereof.

DETAILED DESCRIPTION OF THE INVENTION

1. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic"-(or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR[+] (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroaralkoxy and the like) group may contain one or more substituents. Suitable substituents on the unsaturated carbon atom of an aryl or heteroaryl group are selected from halogen; —Ro; —ORo; —SRo; 1,2-methylenedioxy; 1,2-ethylenedioxy; phenyl (Ph) optionally substituted with Ro; —O(Ph) optionally substituted with Ro; —(CH$_2$)$_{1-2}$(Ph), optionally substituted with Ro; —CH=CH(Ph), optionally substituted with Ro; —NO$_2$; —CN; —N(Ro)$_2$; —NRoC(O)Ro; —NRoC(S)Ro; —NRoC(O)N(Ro)$_2$; —NRoC(S)N(R°)$_2$; —NRoCO$_2$Ro; —NRoNRoC(O)Ro; —NRoNRoC(O)N(Ro)$_2$; —NRoNRoCO$_2$Ro; —C(O)C(O)Ro; —C(O)CH$_2$C(O)Ro; —CO$_2$Ro; —C(O)Ro; —C(S)Ro; —C(O)N(Ro)$_2$; —C(S)N(Ro)$_2$; —OC(O)N(Ro)$_2$; —OC(O)Ro; —C(O)N(ORo)Ro; —C(NORo)Ro; —S(O)$_2$Ro; —S(O)$_3$Ro; —SO$_2$N(Ro)$_2$; —S(O)Ro; —NRoSO$_2$N(Ro)$_2$; —NRoSO$_2$Ro; —N(ORo)Ro; —C(=NH)—N(Ro)$_2$; or —(CH$_2$)$_{0-2}$NHC(O)Ro wherein each independent occurrence of Ro is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of Ro, on the same substituent or different substituents, taken together with the atom(s) to which each Ro group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of Ro are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of Ro is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of Ro (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of Ro (or R$^+$, or any other variable similarly defined herein) are taken together with the atom(s) to which each variable is bound include, but are not limited to the following: a) two independent occurrences of Ro (or R$^+$, or any other variable similarly defined herein) that are bound to the same atom and are taken together with that atom to form a ring, for example, N(Ro)$_2$, where both occurrences of Ro are taken together with the nitrogen atom to form a piperidin-1-yl, piperazin-1-yl, or morpholin-4-yl group; and b) two independent occurrences of Ro (or R$^+$, or any other variable similarly defined herein) that are bound to different atoms and are taken together with both of those atoms to form a ring, for example where a phenyl group is substituted with two occurrences of OR°

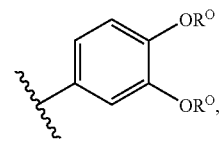

these two occurrences of Ro are taken together with the oxygen atoms to which they are bound to form a fused 6-membered oxygen containing ring

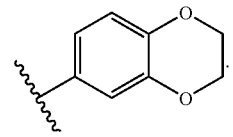

It will be appreciated that a variety of other rings can be formed when two independent occurrences of Ro (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

2. General Description of the Compounds of the Invention

Embodiment 1:

According to one embdoment, the present invention relates to a compound of formula I:

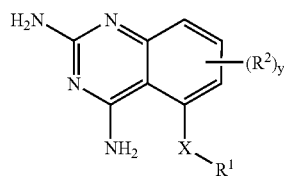

or a pharmaceutically acceptable salt thereof, wherein:
X is O or S;
$R^1$ is a group selected from $C_{1-6}$ aliphatic group, $C_{6-10}$ aryl ring, heteroaryl ring having 5-10 ring atoms, or heterocyclyl ring having 3-10 ring atoms, each optionally substituted with 0-5 occurrences of $TR^3$;
$R^2$ is $QR^4$;
wherein T and Q are each independently a bond or is a $C_1$-$C_6$ alkylidene chain wherein up to two methylene units of T or Q are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR—, —NRCO—, —S—, —SO—, —SO$_2$—, —NR—, —SO$_2$NR—, or —NRSO$_2$—; and each occurrence of $R^3$ or $R^4$ is independently R', halogen, NO$_2$, or CN, or two occurrences of $TR^3$ or $QR^4$, taken together with their intervening atoms form an optionally substituted 3-8 membered saturated, partially unsaturated, or fully unsaturated ring having 0-4 heteroatoms independently selected from nitrogen, oxygen, or sulfur;
wherein R is independently hydrogen or an optionally substituted $C_{1-6}$ aliphatic group;
R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms; and
y is 0, 1, 2 or 3.

In certain embodiments, for compounds of formula I, y is 1, 2, or 3 if $R^1$ is optionally substituted phenyl.

In certain other embodiments, for compounds of formula I, if X is S, and $R^1$ is 4-$^t$Bu-phenyl, and y is 1, then $R^2$ is not NH$_2$, iBuO, OEt, CN or NO$_2$.

As described generally above for compounds of formula I, X is O or S, and thus compounds have the structure as depicted in formula I-A or I-B:

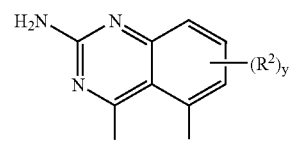

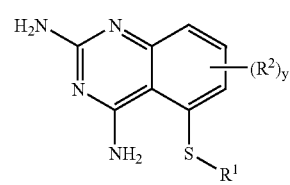

In other preferred embodiments, for compounds of general formula I, or for compounds of formula I-A, or I-B, $R^1$ is a $C_{6-10}$ aryl ring, heteroaryl ring having 5-10 ring atoms, or heterocyclyl ring having 3-10 ring atoms, each optionally substituted with 0-5 occurrences of $TR^3$. In other preferred embodiments, $R^1$ is a group selected from phenyl, pyridyl, pyrimidinyl, naphthyl, cyclohexyl, cyclopentyl, cyclobutyl, or cyclopropyl, each optionally substituted with one or more occurrences of $TR^3$.

In most preferred embodiments, $R^1$ is an optionally substituted phenyl group and compounds have the structure II-A or II-B:

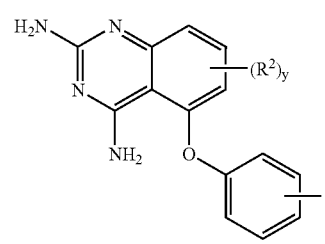

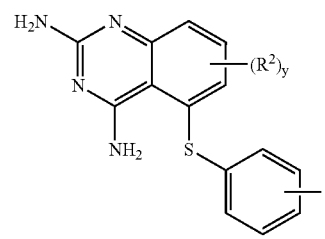

As described generally above, for compounds of formulas I, I-A, I-B, II-A, or II-B, the quinazoline ring can be substituted with up to three independent occurrences of $R^2$. In preferred embodiments, y is 0-2. When the quinazoline ring is substituted (y is 1-3), preferred $R^2$ groups are halogen, CN, NO$_2$, or an optionally substituted group selected from $C_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In other preferred embodiments, y is 0 and the quinazoline ring is unsubstituted. In more preferred embodiments, $R^2$ groups, when present, are each independently NO$_2$, Cl, Br, F, CF$_3$, Me, Et, CN, —COOH, —N(CH₃)₂, —N(Et)₂, —N(iPr)₂, —O(CH₂)₂ OCH₃, —CONH₂, —COOCH₃, —OH, —CH₂OH, —NHCOCH₃, —SO₂NH₂, piperidinyl, piperizinyl, morpholino, or an optionally substituted group selected from $C_{1-4}$alkoxy, phenyl, phenyloxy, benzyl, or benzyloxy. Most preferred $R^2$ groups include those shown below in Table 1.

Additionally, for compounds of formulas I, I-A, I-B, II-A, or II-B, $R^1$ can be substituted with up to five independent occurrences of $TR^3$. In preferred embodiments, x is 0-2. When $R^1$ is substituted (x is 1-5), preferred $TR^3$ groups are halogen, CN, NO₂, or an optionally substituted group selected from $C_{1-4}$alkyl, aryl, aralkyl, —N(R')₂, —CH₂N(R')₂, —OR', —CH₂OR', —SR', —CH₂SR', —COOR', —NRCOR', —CON(R')₂, or —S(O)₂N(R')₂. In other preferred embodiments, x is 0 and $R^1$ is unsubstituted. In more preferred embodiments, $TR^3$ groups, when present, are each independently NO₂, Cl, Br, F, CF₃, Me, Et, CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, piperidinyl, piperizinyl, morpholino, or an optionally substituted group selected from $C_{1-4}$alkoxy, phenyl, phenyloxy, benzyl, or benzyloxy. Most preferred $TR^3$ groups include those shown below in Table 1.

In certain exemplary embodiments, compounds of formula II-A or II-B are provided:

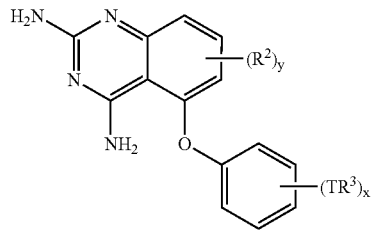

II-A

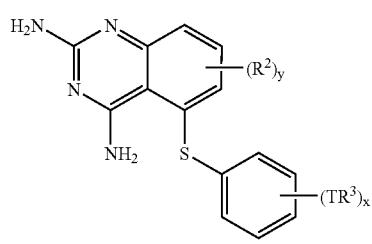

II-B wherein y is 0 or 1, and R groups, when present, are NO₂, Cl, Br, F, CF₃, Me, Et, CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, piperidinyl, piperizinyl, morpholino, or an optionally substituted group selected from $C_{1-4}$alkoxy, phenyl, phenyloxy, benzyl, or benzyloxy; and x is 0, 1, or 2, and $TR^3$ groups, when present, are each independently NO₂, Cl, Br, F, CF₃, Me, Et, CN, —COOH, —N(CH₃)₂, —N(Et)₂, —N(iPr)₂, —O(CH₂)₂ OCH₃, —CONH₂, —COOCH₃, —OH, —CH₂OH, —NHCOCH₃, —SO₂NH₂, piperidinyl, piperizinyl, morpholino, or an optionally substituted group selected from $C_{1-4}$alkoxy, phenyl, phenyloxy, benzyl, or benzyloxy.

TABLE 1

Examples of Compounds of Formula I:

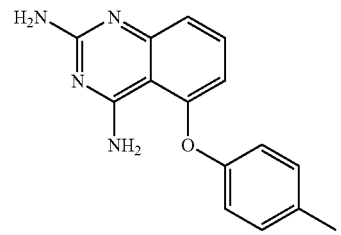

I-1

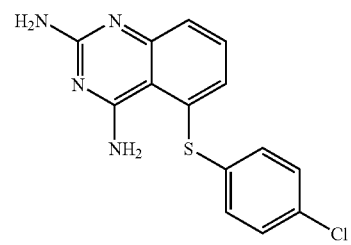

I-2

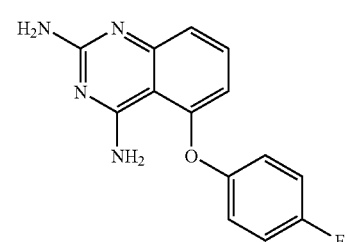

I-3

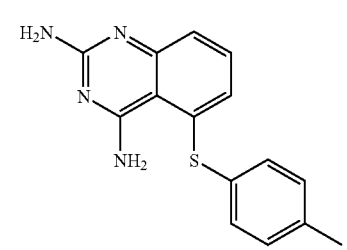

I-4

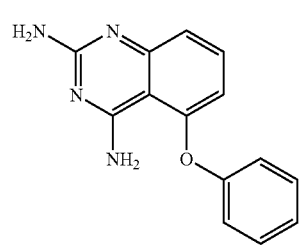

I-5

I-6

TABLE 1-continued

Examples of Compounds of Formula I:

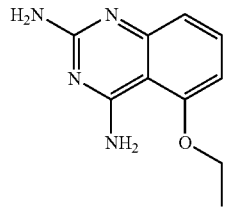

Embodiment 2:

According to another embodiment, the present invention relates to a compound of formula V:

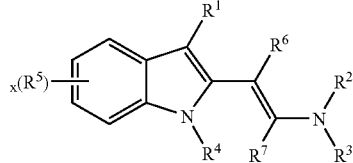

or a pharmaceutically acceptable salt thereof, wherein:
$R^1$ is —(C=O)R' or CN;
$R^2$ and $R^3$ are each independently R', wherein R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms; or $R^2$ and $R^3$ are taken together with the nitrogen atom to which they are bound to form an optionally substituted 3-8 membered saturated, partially unsaturated, or fully unsaturated ring having 0-4 heteroatoms independently selected from nitrogen, oxygen, or sulfur;
$R^4$ is R wherein R is independently hydrogen or an optionally substituted $C_{1-6}$ aliphatic group;
$R^5$ is $TR^8$, wherein wherein T is a bond or is a $C_1$-$C_6$ alkylidene chain wherein up to two methylene units of T are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR, —NRCO—, —S—, —SO—, —SO$_2$—, —NR—, —SO$_2$NR—, or —NRSO$_2$—; and each occurrence of $R^8$ is independently R', halogen, NO$_2$, or CN, or two occurrences of $TR^8$, taken together with their intervening atoms form an optionally substituted 3-8 membered saturated, partially unsaturated, or fully unsaturated ring having 0-4 heteroatoms independently selected from nitrogen, oxygen, or sulfur;
$R^6$ and $R^7$ are each independently R; and
x is 0, 1, 2 or 3.

In certain embodiments, for the compounds of formula V as described generally above,
a) when $R^1$ is —(C=O)H, and $R^2$ and $R^3$ are each Me, then:
   i) when $R^4$ is Me, Et, or —CH$_2$Ph, x is 1, $R^5$ is NO$_2$, then $R^6$ and $R^7$ are not simultaneously hydrogen; and
   ii) when $R^4$ is H, and x is 0, then $R^6$ is not CN when $R^7$ is hydogen;

b) when R is CN, $R^2$ and R are each Me, $R^4$ is Me, x is 1, and $R^5$ is NO$_2$, then $R^6$ and $R^7$ are not simultaneously hydrogen.

As described generally above for compounds of formula V, $R^1$ is —(C=O)R' or CN. In certain preferred embodiments of compounds of formula V, $R^1$ is —(C=O)R', where R' is hydrogen, or $R^1$ is CN, and compounds have the structure as depicted in formula V-A or V-B:

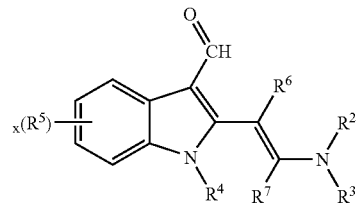

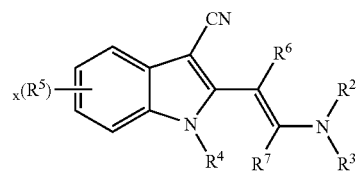

In other preferred embodiments, for compounds of general formula V, or for compounds of formula V-A, or V-B, $R^2$ and $R^3$ are each independently hydrogen or an optionally substituted $C_{1-6}$ aliphatic group. In more preferred embodiments of compounds of formula V-A or formula V-B, one or both of $R^2$ or $R^3$ is an optionally substituted $C_{1-6}$ aliphatic group, wherein the $C_{1-6}$ aliphatic group is preferably substituted with one or more occurrences of halogen; —Ro; —ORo; —SRo; 1,2-methylenedioxy; 1,2-ethylenedioxy; phenyl (Ph) optionally substituted with Ro; —O(Ph) optionally substituted with Ro; —(CH$_2$)$_{1-2}$(Ph), optionally substituted with Ro; —CH=CH(Ph), optionally substituted with Ro; —NO$_2$; —CN; —N(Ro)$_2$; —NRoC(O)Ro; —NRoC(S)Ro; —NRoC(O)N(Ro)$_2$; —NRoC(S)N(Ro)$_2$; —NRoCO$_2$Ro; —NRo NRoC(O)Ro; —NRoNRoC(O)N(Ro)$_2$; —NRoNRoCO$_2$Ro; —C(O)C(O)Ro; —C(O)CH$_2$C(O)Ro; —CO$_2$Ro; —C(O)Ro; —C(S)Ro; —C(O)N(Ro)$_2$; —C(S)N(Ro)$_2$; —OC(O)N(Ro)$_2$; —OC(O)Ro; —C(O)N(ORo)Ro; —C(NORo)Ro; —S(O)$_2$Ro; —S(O)$_3$Ro; —SO$_2$N(Ro)$_2$; —S(O)Ro; —NRoSO$_2$N(R$^9$)$_2$; —NRoSO$_2$Ro; —N(ORo)Ro; —C(=NH)—N(Ro)$_2$; or —(CH$_2$)$_{0-2}$NHC(O)Ro, wherein each independent occurrence of Ro is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of Ro, on the same substituent or different substituents, taken together with the atom(s) to which each Ro group is bound, form a 5-8-membered heterocyclyl, aryl, or heteroaryl ring or a 3-8-membered cycloalkyl ring having 0-3 heteroatoms independently selected from nitrogen, oxygen, or sulfur.

In other preferred embodiments of compounds of formula V-A or formula V-B, one or both of $R^2$ or $R^3$ is H$_3$, —CH$_2$CH$_3$, —(CH$_2$)$_3$CH$_3$, —(CH$_2$)$_4$CH$_3$, —(CH$_2$)$_5$CH$_3$, —C(CH$_3$)$_3$, —CH(CH$_3$)$_2$, —CH$_2$CH(CH$_3$)$_2$, —CH$_2$OH, —CH$_2$CH$_2$OH, —CH$_2$CH$_2$CH$_2$OH, —CH$_2$CH$_2$CH$_2$CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, or —CF$_3$.

As described generally above for compounds of general formula V, or for compounds of formula V-A or V-B, $R^4$ is R wherein R is independently hydrogen or an optionally substituted $C_{1-6}$ aliphatic group. In more preferred embodiments, $R^4$ is an optionally substituted $C_{1-6}$ aliphatic group, wherein the $C_{1-6}$ aliphatic group is preferably substituted with one or more occurrences of halogen; —Ro; —ORo; —SRo; 1,2-methylenedioxy; 1,2-ethylenedioxy; phenyl (Ph) optionally substituted with Ro; —O(Ph) optionally substituted with Ro; —(CH$_2$)$_{1-2}$(Ph), optionally substituted with Ro; —CH=CH (Ph), optionally substituted with Ro; —NO$_2$; —CN; —N(Ro)$_2$; —NRoC(O)Ro; —NRoC(S)Ro; —NRoC(O)N(Ro)$_2$; —NRoC(S)N(Ro)$_2$; —NRoCO$_2$Ro; —NRoNRoC(O)Ro; —NRoNRoC(O)N(Ro)$_2$; —NRoNRoCO$_2$Ro; —C(O)C(O)Ro; —C(O)CH$_2$C(O)Ro; —CO$_2$Ro; —C(O)Ro; —C(S)Ro; —C(O)N(Ro)$_2$; —C(S)N(R°)$_2$; —OC(O)N(Ro)$_2$; —OC(O)Ro; —C(O)N(ORo)Ro; —C(NORo)Ro; —S(O)$_2$Ro; —S(O)$_3$Ro; —SO$_2$N(Ro)$_2$; —S(O)Ro; —NRoSO$_2$N(Ro)$_2$; —NRoSO$_2$Ro; —N(ORo)Ro; —C(=NH)—N(Ro)$_2$; or —(CH$_2$)$_{0-2}$NHC(O)Ro, wherein each independent occurrence of Ro is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of Ro, on the same substituent or different substituents, taken together with the atom(s) to which each Ro group is bound, form a 5-8-membered heterocyclyl, aryl, or heteroaryl ring or a 3-8-membered cycloalkyl ring having 0-3 heteroatoms independently selected from nitrogen, oxygen, or sulfur. In other preferred embodiments, $R^4$ is —CH$_3$, —CH$_2$CH$_3$, —(CH$_2$)$_3$CH$_3$, —(CH$_2$)$_4$CH$_3$, —(CH$_2$)$_5$CH$_3$, —C(CH$_3$)$_3$, —CH(CH$_3$)$_2$, —CH$_2$CH(CH$_3$)$_2$, —CH$_2$OH, —CH$_2$CH$_2$OH, —CH$_2$CH$_2$CH$_2$OH, —CH$_2$CH$_2$CH$_2$CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, or —CF$_3$.

As described generally above, for compounds of formulas V, V-A, or V-B, the indole ring can be substituted with up to four independent occurrences of $R^5$. In preferred embodiments, x is 0-2. When the indole ring is substituted (x is 1-4), preferred $R^5$ groups are halogen, CN, NO$_2$, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In other preferred embodiments, x is 0 and the indole ring is unsubstituted. In more preferred embodiments, $R^5$ groups, when present, are each independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, morpholino, or an optionally substituted group selected from $C_{1-4}$ alkoxy, phenyl, phenyloxy, benzyl, or benzyloxy. Most preferred $R^5$ groups include those shown below in Table 2.

Preferred $R^6$ and $R^7$ groups compounds of formula V are hydrogen and $C_1$-$C_4$ alkyl. In most preferred embodiments, $R^6$ and $R^7$ are each independently hydrogen or methyl.

In one preferred subset, compounds have formula V-A:

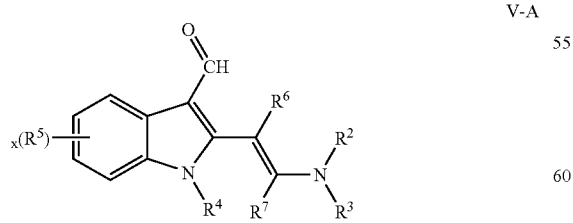

V-A wherein one or both of $R^2$ or $R^3$ is —CH$_3$, —CH$_2$CH$_3$, —(CH$_2$)$_3$CH$_3$, —(CH$_2$)$_4$CH$_3$, —(CH$_2$)$_5$CH$_3$, —C(CH$_3$)$_3$, —CH(CH$_3$)$_2$, —CH$_2$CH(CH$_3$)$_2$, —CH$_2$OH, —CH$_2$CH$_2$OH, —CH$_2$CH$_2$CH$_2$OH, —CH$_2$CH$_2$CH$_2$CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, or —CF$_3$;

$R^4$ is —CH$_3$, —CH$_2$CH$_3$, —(CH$_2$)$_3$CH$_3$, —(CH$_2$)$_4$CH$_3$, —(CH$_2$)$_5$CH$_3$, —C(CH$_3$)$_3$, —CH(CH$_3$)$_2$, —CH$_2$CH(CH$_3$)$_2$, —CH$_2$OH, —CH$_2$CH$_2$OH, —CH$_2$CH$_2$CH$_2$OH, —CH$_2$CH$_2$CH$_2$CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, or —CF$_3$; $R^5$ groups, when present, are each independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, morpholino, or an optionally substituted group selected from $C_{1-4}$ alkoxy, phenyl, phenyloxy, benzyl, or benzyloxy; and $R^6$ and $R^7$ are each independently hydrogen or methyl.

In other preferred subsets for compounds described above for formula V, $R^4$ is CH$_3$ and $R^6$ and $R^7$ are each hydrogen.

TABLE 2

Examples of Compounds of Formula V:

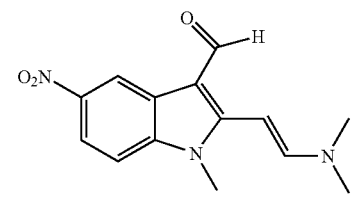

V-1

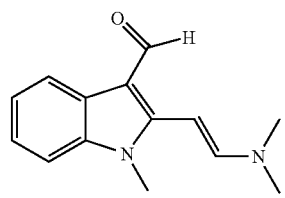

V-2

V-3

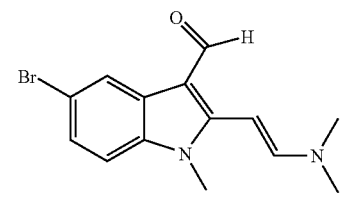

V-4

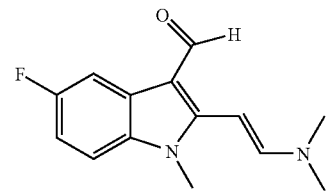

V-5

TABLE 2-continued

Examples of Compounds of Formula V:

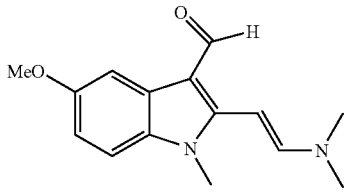

V-6

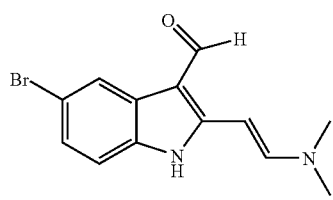

V-7

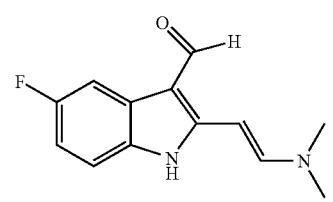

V-8

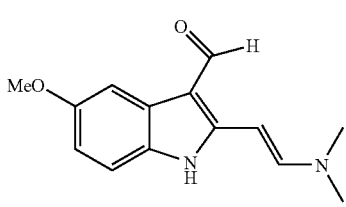

Embodiment 3:

According to one embodiment, the present invention relates to a compound of formula VI:

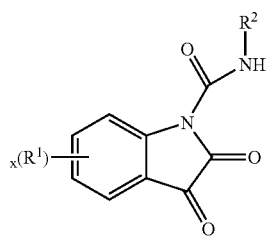

VI or a pharmaceutically acceptable salt thereof, wherein:
$R^1$ is $TR^3$, wherein wherein T is a bond or is a $C_1$-$C_6$ alkylidene chain wherein up to two methylene units of T are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR, —NRCO—, —S—, —SO—, —SO$_2$—, —NR—, —SO$_2$NR—, or —NRSO$_2$—; and each occurrence of $R^3$ is independently R', halogen, NO$_2$, or CN, or two occurrences of $TR^3$, taken together with their intervening atoms form an optionally substituted 3-8 membered saturated, partially unsaturated, or fully unsaturated ring having 0-4 heteroatoms independently selected from nitrogen, oxygen, or sulfur;
x is 0, 1, 2, or 3;
$R^2$ is an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms;
wherein R is independently hydrogen or an optionally substituted $C_{1-6}$ aliphatic group;
and R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms.

As described generally above for compounds of formula VI, $R^1$ is $TR^3$, wherein wherein T is a bond or is a $C_1$-$C_6$ alkylidene chain wherein up to two methylene units of T are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR, —NRCO—, —S—, —SO—, —SO$_2$—, —NR—, —SO$_2$NR—, or —NRSO$_2$—; and each occurrence of $R^3$ is independently R', halogen, NO$_2$, or CN, or two occurrences of $TR^3$, taken together with their intervening atoms form an optionally substituted 3-8 membered saturated, partially unsaturated, or fully unsaturated ring having 0-4 heteroatoms independently selected from nitrogen, oxygen, or sulfur, and x is 0, 1, 2, or 3. In preferred embodiments, x is 1 and compounds have the general structure VI-A:

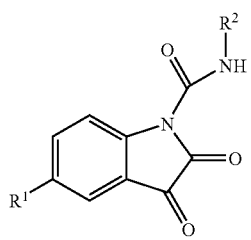

VI-A

In certain exemplary embodiments of formula VI, preferred $R^1$ groups are hydrogen, halogen, CN, NO$_2$, or an optionally substituted group selected from $C_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In other preferred embodiments, x is 0 and the ring is unsubstituted (e.g., hydrogen). In more preferred embodiments, $R^1$ groups, when present, are each independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, morpholino, or an optionally substituted group selected from $C_{1-4}$alkoxy, phenyl, phenyloxy, benzyl, or benzyloxy. Most preferred $R^1$ groups include those shown below in Table 3.

As described generally above for compounds of formula VI, $R^2$ is an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms. In certain preferred embodiments R is an optionally substituted group selected from cyclohexyl, cyclopentyl, cyclobutyl, cyclopropyl, phenyl, naphthyl, $C_{1-6}$alkyl, pyridyl, and pyrimidinyl. In most preferred embodiments, $R^2$ is optionally substituted cyclohexyl.

In certain preferred embodiments of formula VI, $R^2$ is optionally substituted with one or more occurrences of halogen; —Ro; —ORo; —SRo; 1,2-methylenedioxy; 1,2-ethylenedioxy; phenyl (Ph) optionally substituted with Ro; —O(Ph) optionally substituted with Ro; —(CH$_2$)$_{1-2}$(Ph), optionally substituted with Ro; —CH═CH(Ph), optionally substituted with Ro; —NO$_2$; —CN; —N(Ro)$_2$; —NRoC(O)Ro; —NRoC(S)Ro; —NRoC(O)N(Ro)$_2$; —NR°C(S)N(Ro)$_2$; —NRoCO$_2$Ro; —NRo NRoC(O)Ro; —NRoNRoC(O)N(Ro)$_2$; —NRoNRoCO$_2$Ro; —C(O)C(O)Ro; —C(O)CH$_2$C(O)Ro; —CO$_2$Ro; —C(O)Ro; —C(S)Ro; —C(O)N(Ro)$_2$; —C(S)N(Ro)$_2$; —OC(O)N(Ro)$_2$; —OC(O)Ro; —C(O)N(ORo)Ro; —C(NORo)Ro; —S(O)$_2$Ro; —S(O)$_3$R'; —SO$_2$N(Ro)$_2$; —S(O)Ro; —NRoSO$_2$N(Ro)$_2$; —NRoSO$_2$Ro; —N(ORo)Ro; —C(═NH)—N(Ro)$_2$; or —(CH$_2$)$_{0-2}$NHC(O)Ro, wherein each independent occurrence of Ro is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of Ro, on the same substituent or different substituents, taken together with the atom(s) to which each Ro group is bound, form a 5-8-membered heterocyclyl, aryl, or heteroaryl ring or a 3-8-membered cycloalkyl ring having 0-3 heteroatoms independently selected from nitrogen, oxygen, or sulfur.

In most preferred embodiments of formula VI, $R^2$ is optionally substituted with one or more occurrences of halogen; $C_{1-4}$alkyl, N(Ro)$_2$; —ORo; —SRo; NO$_2$, or CN.

TABLE 3

Examples of Compounds of Formula VI:

VI-1

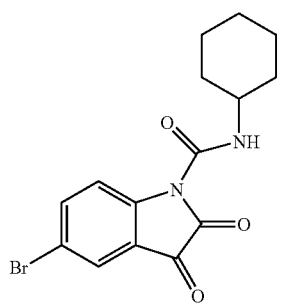

VI-2

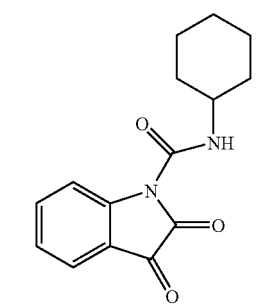

TABLE 3-continued

Examples of Compounds of Formula VI:

VI-3

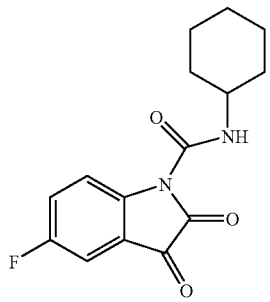

VI-4

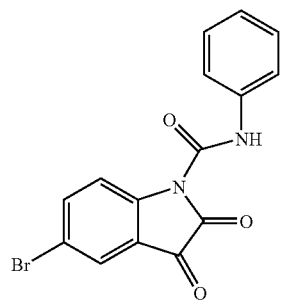

VI-5

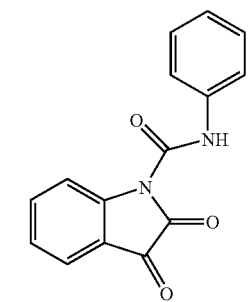

VI-6

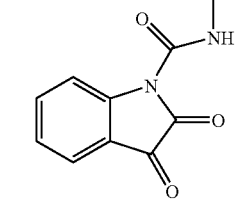

Embodiment 4:

According to one embodiment, the present invention relates to a compound of formula VII:

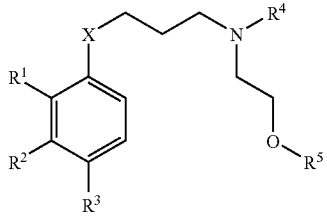

VII or a pharmaceutically acceptable salt thereof, wherein:

X is O or S;

$R^1$, $R^2$, and $R^3$ are each independently is $Th^x$, wherein wherein T is a bond or is a $C_1$-$C_6$ alkylidene chain wherein up to two methylene units of T are optionally replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR—, —NRCO—, —S—, —SO—, —SO$_2$—, —NR—, —SO$_2$NR—, or —NRSO$_2$—; and each occurrence of $R^x$ is independently R', halogen, NO$_2$, or CN, or two occurrences of $TR^x$, taken together with their intervening atoms form an optionally substituted 3-8 membered saturated, partially unsaturated, or fully unsaturated ring having 0-4 heteroatoms independently selected from nitrogen, oxygen, or sulfur;

wherein R is independently hydrogen or an optionally substituted $C_{1-6}$ aliphatic group;

R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms; and $R^4$ and $R^5$ are each independently hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms.

In certain exemplary embodiments of formula VII, preferred $R^1$, $R^2$, and $R^3$ groups are each independently hydrogen, halogen, CN, NO$_2$, or an optionally substituted group selected from $C_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In more preferred embodiments, $R^1$, $R^2$, and $R^3$ groups, when present, are each independently hydrogen, NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, morpholino, or an optionally substituted group selected from $C_{1-4}$alkoxy, phenyl, phenyloxy, benzyl, or benzyloxy. Most preferred $R^1$ groups include those shown below in Table 4.

As described generally above for compounds of formula VII, $R^4$ and $R^5$ are each independently hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms. In certain preferred embodiments, $R^4$ is hydrogen or $C_{1-4}$alkyl. In certain preferred embodiments $R^5$ is an optionally substituted group selected from hydrogen, $C_{1-4}$alkyl, cyclohexyl, cyclopentyl, cyclobutyl, cyclopropyl, phenyl, naphthyl, $C_{1-6}$alkyl, pyridyl, and pyrimidinyl.

In certain preferred embodiments of formula VII, $R^4$ and $R^5$ are each optionally substituted with one or more occurrences of halogen; —Ro; —ORo; —SRo; 1,2-methylenedioxy; 1,2-ethylenedioxy; phenyl (Ph) optionally substituted with Ro; —O(Ph) optionally substituted with Ro; —(CH$_2$)$_{1-2}$(Ph), optionally substituted with Ro; —CH=CH(Ph), optionally substituted with Ro; —NO$_2$; —CN; —N(Ro)$_2$; —NRoC(O)Ro; —NRoC(S)Ro; —NRoC(O)N(R')$_2$; —NRoC(S)N(Ro)$_2$; —NRoCO$_2$Ro; —NRo NRoC(O)Ro; —NRoNRoC(O)N(Ro)$_2$; —NRoNR°CO$_2$Ro; —C(O)C(O)Ro; —C(O)CH$_2$C(O)Ro; —CO$_2$Ro; —C(O)Ro; —C(S)Ro; —C(O)N(Ro)$_2$; —C(S)N(R°)$_2$; —OC(O)N(Ro)$_2$; —OC(O)Ro; —C(O)N(ORo)Ro; —C(NORo)Ro; —S(O)$_2$Ro; —S(O)$_3$ Ro; —SO$_2$N(Ro)$_2$; —S(O)Ro; —NRoSO$_2$N(Ro)$_2$; —NRoSO$_2$Ro; —N(ORo)Ro; —C(=NH)—N(Ro)$_2$; or —(CH$_2$)$_{0-2}$NHC(O)Ro, wherein each independent occurrence of Ro is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of Ro, on the same substituent or different substituents, taken together with the atom(s) to which each Ro group is bound, form a 5-8-membered heterocyclyl, aryl, or heteroaryl ring or a 3-8-membered cycloalkyl ring having 0-3 heteroatoms independently selected from nitrogen, oxygen, or sulfur.

In most preferred embodiments of formula VII, $R^4$ and $R^5$ are each optionally substituted with one or more occurrences of halogen; $C_{1-4}$alkyl, N(Ro)$_2$; —ORo; —SRo; NO$_2$, or CN.

TABLE 4

Examples of Compounds of Formula VII:

VII-1

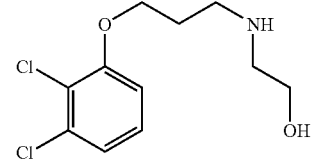

VII-2

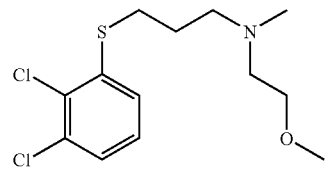

VII-3

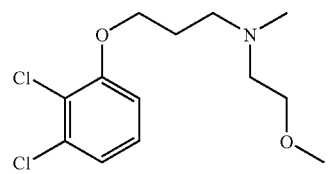

VII-4

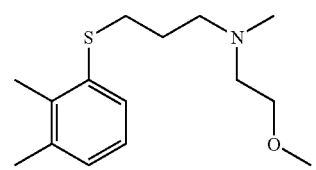

TABLE 4-continued

Examples of Compounds of Formula VII:

VII-5

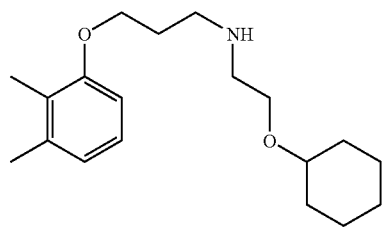

VII-6

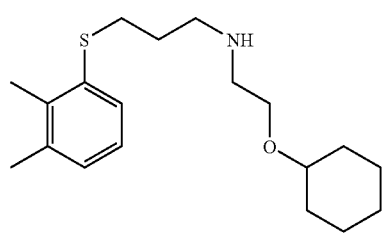

Embodiment 5:

According to one embodiment, the present invention relates to a compound of formula VIII:

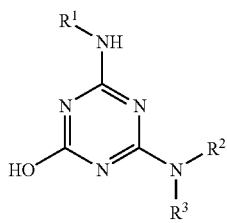

VIII or a pharmaceutically acceptable salt thereof, wherein:
$R^1$, $R^2$ and $R^3$ are each independently a group selected from hydrogen, $C_{1-6}$ aliphatic group, $R^1$ is a $C_{6-10}$ aryl ring, a heteroaryl ring having 5-10 ring atoms, or a heterocyclyl ring having 3-10 ring atoms, each optionally substituted with 0-5 occurrences of $TR^3$, provided that $R^1$, $R^2$, and $R^3$ are not simultaneously hydrogen;
wherein each occurrence of T is independently a bond or is a $C_1$-$C_6$ alkylidene chain wherein up to two methylene units of T or Q are optionally replaced by —C(O)—, —C(O)C(O)—, —CONR—, —CONRNR—, —CO$_2$—, —OC(O)—, —NRCO$_2$—, —O—, —NR-CONR—, —OC(O)NR—, —NRNR, —NRCO—, —S—, —SO—, —SO$_2$—, —NR—, —SO$_2$NR—, or —NRSO$_2$—; and each occurrence of $R^3$ is independently R', halogen, NO$_2$, or CN, or two occurrences of $TR^3$ taken together with their intervening atoms form an optionally substituted 3-8 membered saturated, partially unsaturated, or fully unsaturated ring having 0-4 heteroatoms independently selected from nitrogen, oxygen, or sulfur;

wherein R is independently hydrogen or an optionally substituted $C_{1-6}$ aliphatic group; and
R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms.

In preferred embodiments of formula VIII, $R^1$ is a $C_3$-$C_6$ cycloaliphatic group, a $C_{6-10}$ aryl ring, a heteroaryl ring having 5-10 ring atoms, or a heterocyclyl ring having 3-10 ring atoms, each optionally substituted with 0-5 occurrences of $TR^3$. In other preferred embodiments, $R^1$ is a group selected from phenyl, pyridyl, pyrimidinyl, naphthyl, cyclohexyl, cyclopentyl, cyclobutyl, or cyclopropyl, each optionally substituted with one or more occurrences of $Th^3$.

In certain other preferred embodiments, $R^1$ is an optionally substituted cyclopentyl group and compounds have the structure of formula VIII-A:

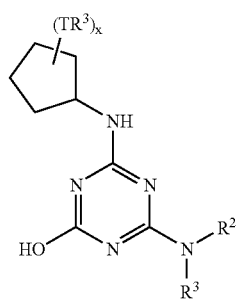

VIII-A wherein x is 0-2.

In other preferred embodiments, for compounds of general formula VIII, or for compounds of formula VIII-A, $R^2$ and $R^3$ are each independently hydrogen or an optionally substituted $C_{1-6}$ aliphatic group. In more preferred embodiments, one or both of $R^2$ or $R^3$ is an optionally substituted $C_{1-6}$aliphatic group, wherein the $C_{1-6}$ aliphatic group is preferably substituted with one or more occurrences of $TR^3$.

In other preferred embodiments of formula VIII, one or both of $R^2$ or $R^3$ is —CH$_3$, —CH$_2$CH$_3$, —(CH$_2$)$_3$CH$_3$, —(CH$_2$)$_4$CH$_3$, —(CH$_2$)$_5$CH$_3$, —C(CH$_3$)$_3$, —CH(CH$_3$)$_2$, —CH$_2$CH(CH$_3$)$_2$, —CH$_2$OH, —CH$_2$CH$_2$OH, —CH$_2$CH$_2$CH$_2$OH, —CH$_2$CH$_2$CH$_2$CH$_2$OH, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CF$_3$, —CH$_2$phenyl, —CH$_2$CH$_2$phenyl, or —CH$_2$CH$_2$CH$_2$phenyl, wherein the phenyl group is optionally substituted with one or more occrrences of halogen, NO$_2$, CN, R', —OR'; —N(R')$_2$, or —SR'.

Additionally, for compounds of formulae VIII or VIII-A, $R^1$ can be substituted with up to five independent occurrences of $TR^3$. In preferred embodiments, x is 0-2. When $R^1$ is substituted (x is 1-5), preferred $TR^3$ groups are halogen, CN, NO$_2$, or an optionally substituted group selected from $C_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$. In other preferred embodiments, x is 0 and $R^1$ is unsubstituted. In more preferred embodiments, $TR^3$ groups, when present, are each independently NO$_2$, Cl, Br, F, CF$_3$, Me, Et, CN, —COOH, —N (CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, morpholino, or an optionally substituted group selected from $C_{1-4}$alkoxy, phenyl, phenyloxy, benzyl, or benzyloxy. Most preferred TR³ groups include those shown below in Table 5.

In certain exemplary embodiments, compounds of formula VIII-A are provided:

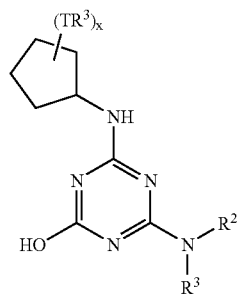

VIII-A wherein x is 0, 1, or 2;

R² and R³ are each independently hydrogen, —CH₃, —CH₂CH₃, —(CH₂)₃CH₃, —(CH₂)₄CH₃, —(CH₂)₅CH₃, —C(CH₃)₃, —CH(CH₃)₂, —CH₂CH(CH₃)₂, —CH₂OH, —CH₂CH₂OH, —CH₂CH₂CH₂OH, —CH₂CH₂CH₂CH₂OH, —CH₂NH₂, —CH₂CH₂NH₂, —CH₂CH₂CH₂NH₂, —CH₂CH₂CH₂CH₂NH₂, —CF₃, —CH₂phenyl, —CH₂CH₂phenyl, or —CH₂CH₂CH₂phenyl, wherein the phenyl group is optionally substituted with one or more occrrences of halogen, NO₂, CN, R', —OR'; —N(R')₂, or —SR'.

TABLE 5

Examples of Compounds of Formula VIII:

VIII-1

VIII-2

VIII-3

TABLE 5-continued

Examples of Compounds of Formula VIII:

VIII-4

VIII-5

VIII-6

3. General Synthetic Methodology:

Embodiment 1:

The compounds of formula I (Embodiment 1) may be prepared in general by methods known to those skilled in the art for analogous quinazoline compounds, as illustrated by U.S. Pat. No. 6,204,267.

Embodiment 2:

Compounds of formula V (Embodiment 2) may be prepared as illustrated below in Scheme I and Scheme II.

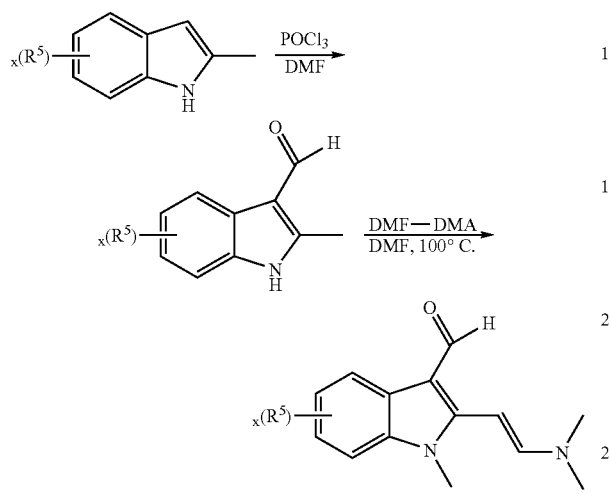

Scheme I above depicts the synthesis of a series of indole analogs produced by a two-step synthesis starting from the commercially available aryl-substituted 2-methyl indole. The Vilsmeyer reaction was utilized to introduce the requisite formyl group at the 3-position of the aromatic indole. The resulting aryl-substituted 3-formyl-2-methylindole was then treated with 4 equivalents of DMF-DMA in DMF at 80° C. for 2 hours, and yielded the methylated (and some unmethylated product).

Scheme II: Synthesis of Compound V-1:

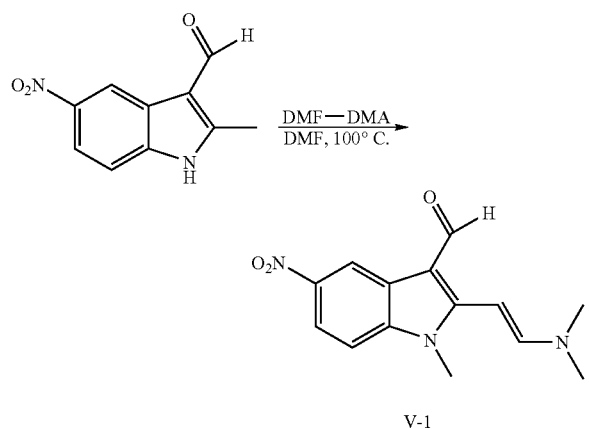

Scheme II above depicts the synthesis of compound V-1 by treating the commercially available 3-formyl-2-methyl-5-nitroindole with 10 equivalents of dimethylformamide dimethylacetal (DMF-DMA) in DMF at 100° C. for 12 hours. The resulting red solid was purified either by RP-HPLC (water/acetonitrile gradient) or by precipitation in ethyl acetate/hexane. Mass and purity were confirmed by LC/MS using a 5 mM ammonium formate pH 6.5/acetonitrile gradient.

Embodiment 3:

The compounds of formula VI (Embodiment 3) may be prepared in general by methods known to those skilled in the art for analogous indole-dione compounds, as illustrated by DE 2306374; Petersen, Siegfried; Heitzer, Helmut; Boron, Liborius. Isatin-N-carboxamides and their reactions. Justus Liebigs Ann. Chem. (1975), Volume Date 1974, (12), 2003-14; and EP 204534.

Embodiment 4:

The compounds of formula VI (Embodiment 4) may be prepared in general by methods known to those skilled in the art for analogous phenyl-propylamine compounds, as illustrated by EP 393574; EP 322390; U.S. Pat. No. 6,051,605; Unangst, Paul C.; Capiris, Thomas; Connor, David T.; and Doubleday, Robert; Heffner, Thomas G.; MacKenzie, Robert G.; Miller, Steven R.; Pugsley, Thomas A.; Wise, Lawrence D. (Aryloxy)alkylamines as Selective Human Dopamine D4 Receptor Antagonists: Potential Antipsychotic Agents. Journal of Medicinal Chemistry (1997), 40(25), 4026-4029.

Embodiment 5:

The compounds of this invention may be prepared in general by methods known to those skilled in the art for analogous triazine compounds, as illustrated generally by Published PCT Application WO03/02544 and U.S. Pat. Appl. Publ. US 2002137747.

Although certain exemplary embodiments are described above and herein, it will be appreciated that compounds of the present invention can be prepared according to the methods described generally above using appropriate starting materials by methods generally available to one of ordinary skill in the art.

4. Uses, Formulation and Administration
Pharmaceutically Acceptable Compositions As discussed above, the present invention provides compounds that are promoters of SMN2, and thus the present compounds are useful for the treatment of neuromuscular disorders such as Spinal Muscular Atrophy. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention th at, upon administration to a recipient, is capable of providing, either directly or indirectly, a compound of this invention or an active metabolite or residue thereof. As used herein, the term "active metabolite or residue thereof" means that a metabolite or residue thereof is also a active as a promoter of the SMN2 gene.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesitable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of neurodegenerative disorders such as Spinal Muscular Atrophy is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for the treatment of Spinal Muscular Atrophy. In certain embodiments, this amount is that amount effective to increase the amount of SMN protein in motor neuron cells. The compounds and compositions, according to the method of the present invention, may be administered using any amount and any route of administration effective for treating or lessening the severity of Spinal Muscular Atrophy. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as promoters of the SMN2 gene, which results in an increase of the total amount of functional SMN messenger RNA (mRNA) and SMN (survival motor neuron) protein in motor neuron cells. Thus, the compounds and compositions of the invention are particularly useful for treating or lessening the severity of a disease, condition, or disorder where a deficiency of the full-length SMN protein is implicated in the disease, condition, or disorder. When a deficiency of the full-length SMN protein is implicated in a particular disease, condition, or disorder, the disease, condition, or disorder may also be referred to as "SMN-deficient disease" or disease symptom. Accordingly, in another aspect, the present invention provides a method for treating or lessening the severity of a disease, condition, or disorder where a deficiency of the full-length SMN protein is implicated in the disease state, e.g., Spinal Muscular Atrophy.

The activity of a compound utilized in this invention as a promoter of SMN2, may be assayed in vitro, in vivo or in a cell line, according to general procedures described herein or as described in Nicole et al. *Muscle & Nerve*, 2002, 4-13; Lefebvre et al. *Human Molecular Genetics* 1998, 7, 1531-1536; Gavrilov et al. *Nature Genetics*, 1998, 20, 230-231; Monani et al., *Human Molecular Genetics* 2000, 9, 333-339; Hsieh-Li et al. *Nature Genetics*, 2000, 24, 66-70); and references cited therein.

The terms "SMN-deficient condition", as used herein, mean any disease or other deleterious condition in which having a deficiency of the SMN protein is known to play a role. The term "SMN-deficient condition" also means those diseases or conditions that are alleviated by treatment with a SMN2 promoter, which is able to increase SMN2 gene transcription, resulting in an increase in the total amount of functional SMN messenger RNA (mRNA) and protein in motor neuron cells. SMN deficient conditions include, but are not limited to, SMAs (Spinal Muscular Atrophy).

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It has also unexpectedly been found that combining compounds of the invention of formula I, with:

1) compounds of formula III:

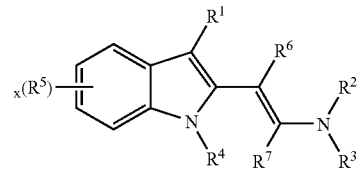

III or a pharmaceutically acceptable salt thereof, wherein:

R is —(C=O)R' or CN;

$R^2$ and $R^3$ are each independently R', wherein R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms; or $R^2$ and $R^3$ are taken together with the nitrogen atom to which they are bound to form an optionally substituted 3-8 membered saturated, partially unsaturated, or fully unsaturated ring having 0-4 heteroatoms independently selected from nitrogen, oxygen, or sulfur;

$R^4$ is R wherein R is independently hydrogen or an optionally substituted $C_{1-6}$ aliphatic group;

$R^5$ is $TR^8$, wherein wherein T is a bond or is a $C_1$-$C_6$ alkylidene chain wherein up to two methylene units of T are optionally replaced by —C(O)—, —C(O)C(O)—, —CONR—, —CONRNR—, —$CO_2$—, —OC(O)—, —$NRCO_2$—, —O—, —NRCONR—, —OC(O)NR—, —NRNR, —NRCO—, —S—, —SO—, —$SO_2$—, —NR—, —$SO_2$NR—, or —$NRSO_2$—; and each occurrence of $R^8$ is independently R', halogen, $NO_2$, or CN, or two occurrences of $TR^8$, taken together with their intervening atoms form an optionally substituted 3-8 membered saturated, partially unsaturated, or fully unsaturated ring having 0-4 heteroatoms independently selected from nitrogen, oxygen, or sulfur;

$R^6$ and $R^7$ are each independently R; and x is 0, 1, 2 or 3; or

2) Sodium Valproate; or 3) compounds of formula IV:

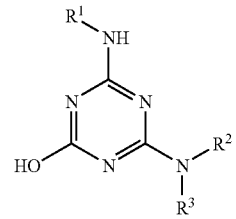

IV or a pharmaceutically acceptable salt thereof, wherein:

$R^1$, $R^2$ and $R^3$ are each independently a group selected from hydrogen, $C_{1-6}$ aliphatic group, $R^1$ is a $C_{6-10}$ aryl ring, a heteroaryl ring having 5-10 ring atoms, or a heterocyclyl ring having 3-10 ring atoms, each optionally substituted with 0-5 occurrences of $TR^3$, provided that $R^1$, $R^2$, and $R^3$ are not simultaneously hydrogen;

wherein each occurrence of T is independently a bond or is a $C_1$-$C_6$ alkylidene chain wherein up to two methylene units of T or Q are optionally replaced by —C(O)—, —C(O)C(O)—, —CONR—, —CONRNR—, —$CO_2$—, —OC(O)—, —$NRCO_2$—, —O—, —NRCONR—, —OC(O)NR—, —NRNR, —NRCO—, —S—, —SO—, —$SO_2$—, —NR—, —$SO_2$NR—, or —$NRSO_2$—; and each occurrence of $R^3$ is independently R', halogen, $NO_2$, or CN, or two occurrences of $TR^3$ taken together with their intervening atoms form an optionally substituted 3-8 membered saturated, partially unsaturated, or fully unsaturated ring having 0-4 heteroatoms independently selected from nitrogen, oxygen, or sulfur;

wherein R is independently hydrogen or an optionally substituted $C_{1-6}$ aliphatic group; and R' is hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms, produces an additive effect (approximately 4-5 fold) on the mRNA levels, as measured by the assays described herein.

In preferred embodiments, compounds of the invention of formula I, with compounds of formula III described directly above are utilized in combination to promote SMN2 activity, to increase SMN protein levels in motor neuron cells, and for the treatment of Spinal Muscular Atrophy.

In most preferred embodiments, compounds of the invention of formula I with a compound having the structure:

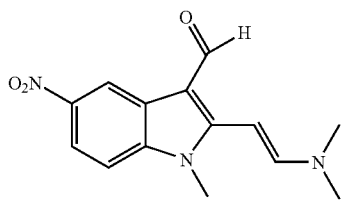

III-A are utilized in combination to promote SMN2 activity, to increase SMN protein levels in motor neuron cells, and for the treatment of Spinal Muscular Atrophy.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids-or combinations thereof to impart controlled release characteristics in the composition.

Another aspect of the invention relates to promoting SMN2 activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Promotion of SMN2 activity in a biological sample is useful for a variety of purposes that are known to one of skill in the art. Examples of such purposes include, but are not limited to, biological specimen storage, and biological assays.

EXAMPLES

Example 1

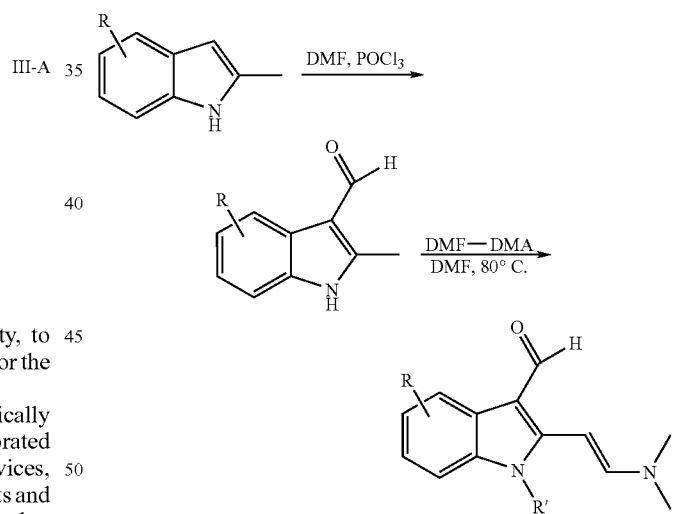

2-((E)-2-(dimethylamino)vinyl)-5-fluoro-1-methyl-1H-indole-3-carbaldehyde (a) Dry DMF (0.6 mL) was added slowly to $POCl_3$ (0.9 mL) at room temperature under nitrogen atmosphere, and the mixture stirred for 5 minutes. 5-fluoro-2-methyl-1H-indole (149 mg, 1.0 mmol) was dissolved in 5 mL dry DMF and added slowly to the rapidly stirring mixture to keep the temperature below 35° C. After stirring for 2 h at room temperature, the reaction mixture was poured into 30 mL ice water. The aqueous layer was basified (30 mL 1.0 N NaOH) and extracted into methylene chloride. The organic layer was washed with water (1×50 mL), brine (1×50 mL), and dried over Na$_2$SO$_4$. The solvent was removed in vacuo to yield an off-white solid. The solid was brought up in 1:3 MeOH/methylene chloride and filtered through a short plug of silica to remove colored impurities. The dried-down solid was then washed with dry acetonitrile to provide the product 5-fluoro-2-methyl-1H-indole-3-carbaldehyde as a crystalline white solid (105 mg, 55% yield) after drying. $^1$H NMR (400 mHz, DMSO-d$_6$) δ 12.10 (s, 1H), 10.03 (s, 1H), 7.72 (dd, J=9.7, 2.6 Hz, 1H), 7.38 (dd, J=8.8, 4.5 Hz, 1H), 7.01 (dt, J=9.2, 2.6 Hz, 1H), 3.34 (s, 1H), 2.68 (s, 3H).

(b) 5-fluoro-2-methyl-1H-indole-3-carbaldehyde (50 mg, 0.28 mmol) was dissolved in 3 mL dry DMF, followed by the addition of N,N-dimethylformamide dimethyl acetal (124 mg, 138 µL, 1.04 mmol). The reaction mixture was heated to 80° C. for 4 h and turned from light yellow to dark red over the course of the reaction. The crude reaction was concentrated in vacuo, dissolved in 0.5 mL DMSO/MeOH, and purified by reverse phase HPLC (5-95% water/acetonitrile gradient over 60 minutes) to obtain 2-((E)-2-(dimethylamino)vinyl)-5-fluoro-1-methyl-1H-indole-3-carbaldehyde as a pale yellow solid (40 mg, 62% yield). $^1$H NMR (400 mHz, DMSO-d$_6$) δ 9.73 (s, 1H), 7.73 (dd, J=9.8, 2.6 Hz, 1H), 7.39 (m, 2H), 6.96 (dt, J=9.2, 2.6 Hz, 1H), 5.20 (d, J=13.1 Hz, 1H), 3.66 (s, 3H), 2.99 (s, 6H). Mass and purity were confirmed by LC/MS using an acetonitrile gradient with 5 mM ammonium formate pH 6.5. Theoretical (M+H)$^+$ m/z for C$_{14}$H$_{15}$FN$_2$O=247.12; Found 247.06.

(c) 2-((E)-2-(dimethylamino)vinyl)-5-fluoro-1H-indole-3-carbaldehyde was also isolated from the crude reaction mixture and obtained as a light yellow solid (10 mg, 15%). Theoretical (M+H)$^+$ m/z for C$_{13}$H$_{13}$FN$_2$O=233.25; Found 233.07. Reduced reaction time and fewer equivalents of DMF-DMA resulted in the preferred formation of this N-desmethyl product.

Example 2

2-((E)-2-(dimethylamino)vinyl)-1-methyl-5-nitro-1H-indole-3-carbaldehyde 5-nitro-2-methyl-1H-indole-3-carbaldehyde (200 mg, 0.98 mmol) was dissolved in 5 mL dry DMF, followed by the addition of N,N-dimethylformamide dimethyl acetal (467 mg, 521 µL, 3.92 mmol). The reaction mixture was heated to 100° C. for 2 h and turned from light yellow to dark red over the course of the reaction. The crude reaction was concentrated in vacuo to obtain a red solid. The crude solid was washed with 5:1 EtOAc/hexane (6×10 mL), followed by hexane (2×10 mL) to obtain 2-((E)-2-(dimethylamino)vinyl)-1-methyl-5-nitro-1H-indole-3-carbaldehyde as a brick red solid (215 mg, 85% yield). Mass and purity were confirmed by LC/MS using an acetonitrile gradient with 5 mM ammonium formate pH 6.5. Theoretical (M+H)$^+$ m/z for C$_{14}$H$_{15}$N$_3$O$_3$=273.11; Found 274.00. $^1$H NMR (400 mHz, DMSO-d$_6$) δ 9.80 (s, 1H), 8.03 (dd, J=8.9, 2.4 Hz, 1H), 7.58 (d, J=9.0 Hz, 1H), 7.58 (m, 2H), 5.25 (d, J=13.0 Hz, 1H), 3.72 (s, 3H), 3.03 (s, 6H).

Example 3

5-bromo-2-((E)-2-(dimethylamino)vinyl)-1-methyl-1H-indole-3-carbaldehyde

Theoretical (M+H)+m/z for C$_{14}$H$_{15}$BrN$_2$O=307.04; Found 306.98.

Example 4

5-bromo-2-((E)-2-(dimethylamino)vinyl)-1H-indole-3-carbaldehyde

Theoretical (M+H)$^+$m/z for C$_{13}$H$_{13}$BrN$_2$O=293.02; Found 292.98.

Example 5

2-((E)-2-(dimethylamino)vinyl)-5-methoxy-1-methyl-1H-indole-3-carbaldehyde

Theoretical (M+H)$^+$m/z for C$_{15}$H$_{18}$N$_2$O$_2$=259.14; Found 259.11.

Example 6

2-((E)-2-(dimethylamino)vinyl)-5-methoxy-1H-indole-3-carbaldehyde

Theoretical (M+H)+m/z for C$_{14}$H$_{16}$N$_2$O$_2$=245.12; Found 245.09.

Example 7

2-((E)-2-(dimethylamino)vinyl)-1-methyl-1H-indole-3-carbaldehyde

Theoretical (M+H)$^+$ m/z for C$_{14}$H$_{16}$N$_2$O=229.13; Found 229.08

Example 8

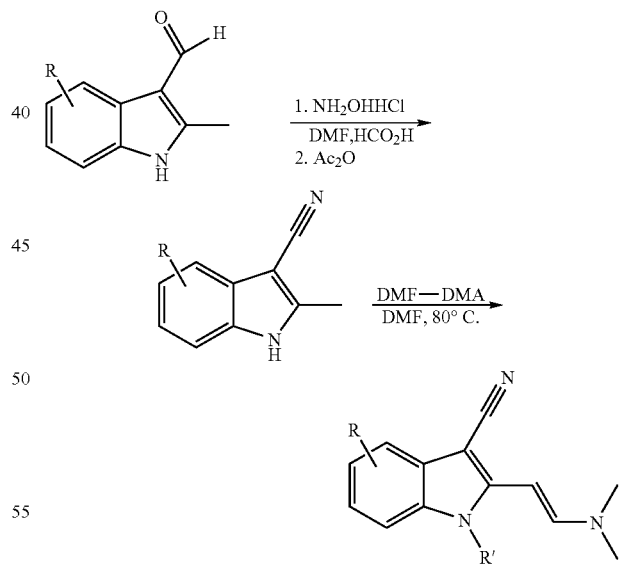

2-((E)-2-(dimethylamino)vinyl)-1-methyl-5-nitro-1H-indole-3-carbonitrile 2-methyl-5-nitro-1H-indole-3-carbaldehyde (375 mg, 1.84 mmol) and hydroxylamine hydrochloride (380 mg, 5.52 mmol) were suspended in formic acid (10 mL) and DMF (3 mL), and heated at 80° C. until the solution had turned dark orange (30 min). Quantitative conversion to the aldoxime intermediate was confirmed by LC/MS. 4 mL of acetic anhydride were added and heating was continued for 1 h. The reaction solution was diluted with cold water (20 mL), and the product extracted into EtOAc. The organic layer was washed with water (2×50 mL), brine (2×50 mL), dried over $MgSO_4$, and filtered. The solvent was removed in vacuo to yield 2-methyl-5-nitro-1H-indole-3-carbonitrile as an ochre-colored solid (330 mg, 89% yield). Mass and purity were confirmed by LC/MS using an acetonitrile gradient with 0.035% TFA/water. Theoretical $(M+H)^+$ m/z for $C_{10}H_7N_3O_2$=202.05; Found 202.2.

2-methyl-5-nitro-1H-indole-3-carbonitrile (200 mg, 0.98 mmol) was dissolved in DMF (4 mL) followed by the addition of N,N-dimethylformamide dimethyl acetal (452 mg, 505 µL, 3.8 mmol). The mixture was heated at 80° C. for 0.5 h and turned from amber-colored to dark red over the course of the reaction. The solvent was removed in vacuo and the crude solid was washed with 5:1 EtOAc/hexane (6×10 mL), followed by hexane (2×10 mL) to obtain 2-((E)-2-(dimethylamino)vinyl)-1-methyl-5-nitro-1H-indole-3-carbonitrile as a dark burgundy solid (235 mg, 89% yield) after drying. Mass and purity were confirmed by LC/MS using an acetonitrile gradient with 5 mM ammonium formate pH 6.5. Theoretical $(M+H)^+$ m/z for $C_{14}H_{14}N_4O_2$=271.11; Found 271.07. $^1H$ NMR (400 mHz, DMSO-$d_6$) δ 8.12 (d, J=2.2 Hz, 1H), 7.99 (dd, J=9.0, 2.3 Hz, 1H), 7.72 (d, J=13.3 Hz, 1H), 7.61 (d, J=9.0 Hz, 1H), 5.17 (d, J=13.3 Hz, 1H), 3.73 (s, 3H), 3.00 (s, 6H).

Example 9

SMN2 Promoter Assay

Compounds were screened for their ability to increase SMN2 gene transcription. In general the screening method of the invention involves the use of an SMN2 promoter-β-lactamase (BLA) assay in NSC-34 cells. The NSC-34 cell line, which exhibits characteristics of motor neurons, is hybrid cell line between mouse spinal cord cells and a mouse neuroblastoma. To generate this assay, a 3.4 kb SMN2 promoter fragment was subcloned into a mammalian expression vector, in which the SMN2 promoter drives beta-lactamase (BLA) expression. This construct was transfected into the NSC-34 cells and a stable pool of SMN2-promoter-BLA cells was generated. This pool was then FACS sorted to isolate single cell clones with low BLA activity, and 15 clones showed a relatively low and uniform level of BLA activity throughout the population. These clones were then further analyzed for increases in transcriptional activity after stimulation with a number of candidate transcriptional regulators, including MNDA, IBMX, retinoic acid, and sodium butyrate. Six of the 15 cell lines showed an increase in BLA activity after sodium butyrate stimulation, while none showed changes in BLA activity after treatment with the other reagents. One clone (SMN2BLAClone11), which showed the highest incease in BLA expression upon sodium butyrate stimulation (1.8 fold), was then selected to optimize the SMN2 promoter BLA assay. Optimized protocols are presented in the procedures below. During the optimization procedures, it was also shown that SMN2BLAClone11 retains motorneuronal properties, such as the expression of choline acetyl-transferase (ChAT) exhibited by the parental cell line in several experimentals. Compounds of the invention were assayed using the procedures detailed above using high throughput screening methods and in general were found to activate the promoter assay. In certain embodiments, compounds activate the promoter assay by approximately 2 fold.

Experimental Protocol for the Subculture and Harvesting of the SMN2 Promoter Assay:

A. Subculture Protocol for and the SMN2minigene-Bla Cell Line (#5.3) and the SMN2 Promoter-Bla Cell Line (#11).

Media: DMEN (Gibco BRL, Cat # 12430-054); 5% FCS (Gibco BRL Cat. # 16140-071); 1×Pen/Strep (Gibco BRL Cat. #15140-122); Optional: G418 500 µg/ml.

Procedure:
a. Cells were kept at a density between 50,000 and 500,000/ml and were fed every three days with DMEM 5% FCS and incubated at 37° C., 5% $CO_2$ and 90% humidity.
b. Cells were then plated at low density (50,000 cells/ml).
c. Cells were then harvested after a minimum of 72 hours, in order to preserve the response to HDAC inhibitors, such as Sodium Butyrate or Trichostatin A.
d. Cells were fed by manually pipetting the cells, and passaging the cells 1 to 10 to a new flask.

B. Standard Assay Protocol #1 for SMN2 Promoter Assays in 96-Well Plates:
e. Cells were washed twice with cold PBS by spinning down and resuspending at 250,000 cells/ml.
f. Cells were resuspended in DMEM 0% FCS at a density of 500,000 cells/ml.
g. Cells were then dispensed 100 µl cells per well of a 96-well, black wall, clear bottom assay plate (Corning Costar, Cat. # 3904). Plate can be pre-formatted with test compounds.
h. The plate was placed at 37° C. for 18 hours.
i. Cells were then removed from the incubator and 20 µl (96-well) 6×CCF2/AM Staining Solution was added that contains probenecid which gives a final concentration of 2 mM. Cells were incubated for 1 hour in the dark at room temperature.

6×CCF2-AM Staining Solution:
60 µl of Sol B
6 µl of CCF2-AM (1 mM)
12 µl of Probenecid (1 M, Sigma, Cat # 8761)
1 µl of Sol C j. Assay plates were read on a fluorimeter (for example, the Cytofluor 4000 from Perceptive Biosystems) using the following two settings: 460/40 nm emission with 395/25 nm excitation, and 530/25 nm emission with 395/25 nm excitation.
k. Raw numbers were subtracted from a media-only blank containing the same amount of CCF2 Staining Solution as the other wells. 460/530 ratios were then calculated from these blank-subtracted values.

C. Standard Assay Protocol #2 for SMN2 Promoter Assays in 96-Well Plates:
l. Cells were washed twice with cold PBS by spinning down and resuspending at 250,000 cells/ml.
m. Cells were then resuspended in DMEM 1% FCS Charcoal Dextran-treated (Hyclone, Cat # SH30038.05) at a density of 5000,000 cells/ml.
n. Cells were then incubated for 24 hours at 37° C.
o. 100 µl cells per well were then dispensed in a 96-well, black wall, clear bottom assay plate (Corning Costar, Cat. # 3904). Plate can be pre-formatted with test compounds.
p. Plate was placed at 37° C. for 18 hours.
q. Cells were removed from the incubator and 20 µl (96-well) 6×CCF2-AM Staining Solution was added that contains Probenecid which gives a final concentration of 2 mM. Cells were incubated for one hour in the dark at room temperature.

6×CCF2-AM Staining Solution:

60 µl of Sol B
6 µl of CCF2-AM (1 mM)
12 µl of Probenecid (1 M, Sigma, Cat# 8761)
1 µl of SolC r. Assay plates were read on a fluorimeter (for example, the Cytofluor 4000 from Perceptive Biosystems) using the following two settings: 460/40 nm emission with 395/25 nm excitation, and 530/25 nm emission with 395/25 nm excitation.

s. Raw numbers were subtracted from a media-only blank containing the same amount of CCF2 Staining Solution as the other wells. 460/530 ratios were then calculated from these blank-subtracted values.

The activity of certain compounds of the invention is shown below:

| Compound | EC50 (uM) |
|---|---|
| I-1 | 0.23 |
| I-2 | 0.53 |
| I-3 | 0.15 |
| I-4 | 0.31 |
| I-5 | 0.25 |
| I-6 | 0.6 |
| V-1 | 6.8 |
| VI-1 | 10 |
| VII-1 | 3 |
| VIII-1 | 9 |

Example 9

Assessment of mRNA Level by RT-PCR Analysis on SMA Patient-Derived Fibroblasts

The ability of compounds of the invention to alter SMN mRNA levels in primary cells derived from two different SMA patients was assessed using a semi-quantitative RT-PCT analysis with two different primer pairs specific to SMN. The first set of primers is located within exon 7 and exon 8 and measures only full-length SMN transcript. The second set is located within exons 4 and 8, and amplifies all SMN transcripts. Transcript ratio was determined by running a portion of the PCR reaction on a 6% polyacrylimide TBE-Urea gel, staining for 20 minutes with Vistra Green nucli acid stain, and quantifying the PCR products using the blue fluorescent detector at a PMT value of 650 to 800 on a Storm Phosphoimager. Compounds of the invention were found to result in an increase of the full-length to delta 7 SMN mRNA ratio by about two-fold.

A) RT-PCT Protocol:

Total RNA was isolated from untreated and treated cells, using the RNeasy Kit (Qiagen) as described by the manufacturer's recommendations. First strand cDNA synthesis was performed with 2 µg of total RNA using an oligo d (T) primer. To amplify endogenous SMN RNA, a multiplex RT-PCT was performed as described in Parsons et al., *American Journal of Human Genetics*, 1998, 63: 1712-1723. Briefly, the following SMN primers were utilized 541C380 (5'-GTGAGAACTC-CAGGTCTCCTGG-3') and 541C1120 (5'-CTACAACAC-CCTTCTCACAG-3') for amplification of exons 4 to 8 of the SMN gene. This can yield four possible RT-PCR products (full length SMN transcript and 3 isoforms lacking exon 5 and/or 7). Amplification of the Hypoxanthine guanine phosphoribosyltransferase gene (HPRT) was performed in a multiplex format as a loading control for the amount of mRNA utilized in the reaction. The following primers specific to the HPRT gene were used: HPRT-for (5'-TGTAATGACCAGT-CAACAGG-3') and HPRT-rev (5'-AATGACTGCTTCT-TACTTTTCT-3'). The cycling conditions were as follows: 95° C. for 5 minutes, 25 cycles of 1 minute at 95° C., 2 minutes at 55° C., 3 minutes at 72° C., and a final extension time of 8 minutes at 72° C. The resulting PCR products were electrophoresed on a 6% polyacrylimide TBE-urea gel, stained for 20 minutes with Vistra Green nuclei acid stain (Pharmacia), and quantified using the blue fluorescent detector at a PMT value of 650 to 800 on a Storm Phosphoimager.

Example 3

Influence of Compound on SMN Protein Levels in Disease Relevant Cells

Compounds of the invention were tested to determine if they increased SMN protein levels, in addition to the levels of full-length SMN mRNA, using Western blotting experiments as detailed below. Compounds of the invention were found to increase protein levels about two-fold.

A) Western Blot Protocol: 2806 Type 1 SMA fibroblast cells were plated at 50,000 to 100,000 cells per 10 cm dish and treated with compound for 48 hours. Media, containing compound, was changed daily and cells were harvested at sub-confluence. The cells were harvested with trypsin, washed two times with PBS, and collected by centrifugation. The resultant cell pellet was re-suspended in 45 µl of RIPA buffer plus protease inhibitors and lysed on ice for 30 minutes. After 30 minutes, 45 µl of NuPAGE LDS sample buffer was added to the sample. 1 ul of reducing agent was then added to 10 µl of each sample and then boiled for 10 minutes. 5 to 10 µl of protein sample was separated on a NuPAGE 10% Bis-Tris gel in 1×NuPAGE MOPS running buffer. The protein was transferred to a PVDF membrane and blocked for one hour at room temperature with TBS containing 5% milk and 0.1% Tween. For each semple, two membranes were prepared, and then each was processed in a different manner. In the first manner, primary antibodies specific to SMN and loading controls were incubated sequentially on the same blot (the first incubation was with anti-SMN antibody (Transduction Labs) for 16 hours at 4° C.; the second incubation was with anti-loading control antibodies (either anti-actin and/or anti-β-tubulin from Sigma) for 1 hour at room temperature). The membrane was next incubated for one hour with an HRP-linked anti-mouse IgG secondary antibody, visualized by chemiluminescence using the ECL Plus kit (Amersham), and quantified using a Storm Phosphoimager. In the second, each blot was cut in half, and the SMN and loading control portions processed separately. The two halves of the blot were incubated for one hour with an HRP-linked anti-mouse IgG secondary antibody, visualized with chemiluminescence using the ECL Plus kit (Amersham), and then these blots were developed on film.

It will be appreciated that certain additional protocols (e.g., in vivo models) for assessing the therapeutic capability of compounds of the invention are known in the art. See, for example, Nicole et al. *Muscle & Nerve*, 2002, 4-13; Lefebvre et al. *Human Molecular Genetics* 1998, 7, 1531-1536; Gavrilov et al. *Nature Genetics*, 1998, 20, 230-231; Monani et al., *Human Molecular Genetics* 2000, 9, 333-339; Hsieh-Li et al. *Nature Genetics*, 2000, 24, 66-70), and references cited therein, the entire contents of which are hereby incorporated by reference.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

10. The method of claim 1, wherein the compound is:
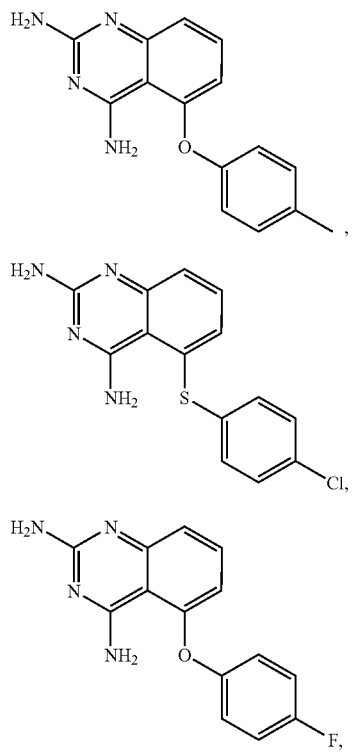

The invention claimed is:

1. A method of treating or ameliorating one or more symptoms produced by Spinal Muscular Atrophy in a patient, comprising the step of administering to said patient a therapeutically effective amount of a compound of formula I:

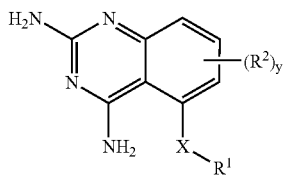

or a pharmaceutically acceptable salt thereof, wherein:
X is O or S;
R$^1$ is a C$_{1-6}$ aliphatic group, C$_{6-10}$ aryl ring, heteroaryl ring having 5-10 ring atoms, or heterocyclyl ring having 3-10 ring atoms, each optionally substituted with 0-5 TR$^3$; wherein each TR$^3$ is independently halogen, CN, NO$_2$, or an optionally substituted C$_{1-4}$ alkyl, aryl, aralkyl, —N(R')$_2$, —CH$_2$N(R')—OR', —Ch$_2$OR', —SR', —CH$_2$SR',—COOR',—NRCOR',—CON(R')$_2$, or —S(O)$_2$N(R')$_2$;
each R$^2$ is independently halogen, CN, NO$_2$, or an optionally substituted C$_{1-4}$ alkyl, aryl, aralkyl, —N(R')$_3$, —CH$_2$N(R')$_2$, —OR', CH$_2$OR', —SR', CH$_2$SR', —COOR', NRCOR', —CON(R')$_2$, or —S(O)$_2$N(R')$_2$;
R' is hydrogen or an optionally substituted C$_{1-6}$ aliphatic group, an optionally substituted C$_{6-10}$ aryl ring, an optionally substituted heteroaryl ring having 5-10 ring atoms, or an optionally substituted heterocyclyl ring having 3-10 ring atoms; and
y is 0, 1, 2 or 3.

2. The method of claim 1, wherein R$^1$ is a C$_{6-10}$ aryl ring, heteroaryl ring having 5-10 ring atoms, or heterocyclyl ring having 3-10 ring atoms, each optionally substituted with 0-5 TR$^3$.

3. The method of claim 1, wherein R$^1$ is phenyl, pyridyl, pyrimidinyl, naphthyl, cyclohexyl, cyclopentyl, cyclobutyl, or cyclopropyl, each optionally substituted with one or more TR$^3$.

4. The method of claim 1, wherein:
R$^1$ is an optionally substituted phenyl group; and
the compound is represented by the structural formula II-A or II-B:

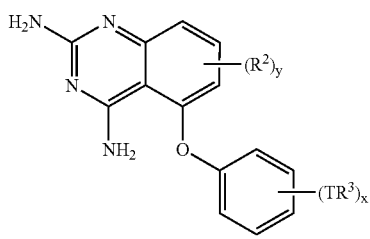

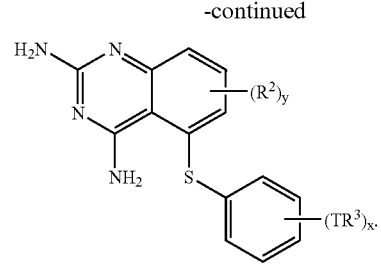

5. The method of claim 1, wherein each R$^2$ is independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, or morpholino, or an optionally substituted C$_{1-4}$ alkoxy, phenyl, phenyloxy, benzyl, or benzyloxy.

6. The method of claim 1, wherein y is 0.

7. The method of claim 1, wherein R$^1$ is unsubstituted.

8. The method of claim 1, wherein each TR$^3$ is independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, piperidinyl, piperizinyl, or morpholino, or an optionally substituted C$_{1-4}$ alkoxy, phenyl, phenyloxy, benzyl, or benzyloxy.

9. The method of claim 1, wherein the compound is represented by structural formula II-A or II-B:

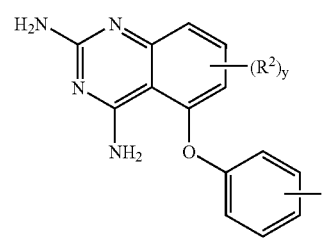

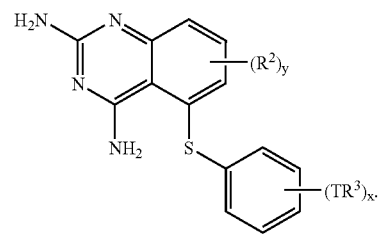

wherein: y is 0 or 1;
each R$^2$ is independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$ OCH$_3$, —CONH$_2$, —COOCH$_3$, —OH, —CH$_2$OH, —NHCOCH$_3$, —SO$_2$NH$_2$, piperidinyl, piperizinyl, or morpholino, or an optionally substituted C$_{1-4}$ alkoxy, phenyl, phenyloxy, benzyl, or benzyloxy;
x is 0, 1, or 2; and
each TR$^3$ is independently NO$_2$, Cl, Br, F, CF$_3$, Me, Et, CN, —COOH, —N(CH$_3$)$_2$, —N(Et)$_2$, —N(iPr)$_2$, —O(CH$_2$)$_2$ OCH$_3$, —CONH$_2$, —COOCH$_3$, —OH, —CH$_2$OH, —NHCOCH$_3$, —SO$_2$NH$_2$, piperidinyl, piperizinyl, or morpholino, or an optionally substituted C$_{1-4}$ alkoxy, phenyl, phenyloxy, benzyl, or benzyloxy.